United States Patent [19]
Jacobs et al.

[11] Patent Number: 5,846,492
[45] Date of Patent: Dec. 8, 1998

[54] SAMPLE QUALITY MEASUREMENT AND/ OR ANALYTE MEASUREMENT IN THE DISPENSING TIP OF AN ANALYZER

[75] Inventors: Merrit Nyles Jacobs, Fairport; Davis Freeman, III, Rochester; James David Shaw, Hilton, all of N.Y.; James Samsoondar; Thomas Moffett, both of Mississauga, Canada

[73] Assignee: Johnson & Johnson Clinical Diagnostics, Inc., Rochester, N.Y.

[21] Appl. No.: 815,451

[22] Filed: Mar. 11, 1997

[51] Int. Cl.[6] .......................... G01N 35/10; G01N 21/01
[52] U.S. Cl. ............................. 422/67; 422/63; 422/64; 422/81; 422/82.05; 422/100; 422/104; 436/43; 436/46; 436/49; 436/50; 436/54; 436/165; 436/171; 436/174; 436/180; 356/244; 356/246; 356/434
[58] Field of Search .................... 422/63, 64, 67, 422/81, 82.05, 100, 104; 436/43, 46, 47, 49, 50, 54, 164, 165, 171, 174, 180; 356/244, 246, 434

[56] References Cited

U.S. PATENT DOCUMENTS

| | | | |
|---|---|---|---|
| 4,252,438 | 2/1981 | Haina et al. | 356/39 |
| 4,318,884 | 3/1982 | Suzuki | 422/63 |
| 4,615,360 | 10/1986 | Jacobs | 141/18 |
| 4,694,173 | 9/1987 | Wong | 250/343 |
| 4,769,216 | 9/1988 | Chandler et al. | 422/58 |
| 4,806,313 | 2/1989 | Ebersole et al. | 422/61 |
| 4,909,992 | 3/1990 | Bjorkman | 422/100 |
| 4,991,958 | 2/1991 | Garner | 356/244 |
| 5,061,632 | 10/1991 | Shepherd et al. | 436/66 |
| 5,079,170 | 1/1992 | Rosman et al. | 436/178 |
| 5,092,674 | 3/1992 | Garner | 356/244 |
| 5,104,218 | 4/1992 | Garner | 356/73 |
| 5,171,537 | 12/1992 | Wainwright et al. | 422/100 |
| 5,343,909 | 9/1994 | Goodman | 141/242 |
| 5,387,526 | 2/1995 | Garner et al. | 436/169 |
| 5,437,979 | 8/1995 | Rampal et al. | 435/6 |
| 5,478,526 | 12/1995 | Sakai et al. | 422/81 |
| 5,512,248 | 4/1996 | Van | 422/100 |
| 5,525,518 | 6/1996 | Lundsgaard et al. | 436/68 |

FOREIGN PATENT DOCUMENTS

0 185 330 A3   12/1985   European Pat. Off. .

*Primary Examiner*—Long V. Le
*Attorney, Agent, or Firm*—Dana M. Schmidt

[57] ABSTRACT

Apparatus and method for detecting patient sample quality, and/or analytes, in the tip used to aspirate the patient sample liquid and then dispense it onto a slide test element. Spectrophotometric analysis is done on the liquid while still in the tip, by scanning the tip for transmittance in a light-tight enclosure, using NIR and adjacent visible radiation, and detecting the absorbence spectra of the liquid. Much smaller liquid volumes, and no through-the-label detection, are required, compared to doing the scanning of the liquid in a primary patient collection container.

4 Claims, 10 Drawing Sheets

SAMPLE QUALITY MEASUREMENT AND/OR ANALYTE MEASUREMENT IN THE DISPENSING TIP OF AN ANALYZER

FIELD OF THE INVENTION

This invention relates to a new use of old apparatus, and a new dispensing station, that allow spectrophotometric analysis to be done on blood samples before they are conventionally tested in a dry or wet assay.

BACKGROUND OF THE INVENTION

Spectrophotometric analysis is commonly applied to many liquids to determine the contents. Such analysis is particularly useful if done with near infrared and adjacent visible radiation, due to the latter's ability to discriminate between a target analyte and other substances.

That such analysis is possible to ascertain hemoglobin, glucose, albumin, lipoproteins, and many other sera components is evident from, e.g., Clin. Chem., Volume 38, Pages 1623–1631 (1992).

Problems have existed, however, in applying such analysis to blood samples to determine the contents or quality of such samples. It has been difficult, for example, to apply it to samples as they are obtained initially, namely in primary patient collection containers. These are usually tubes of varying size that have been centrifuged to separate the liquid serum or plasma from the cellular phases. Such tubes therefore have a) a patient-identification label, b) varying and unpredictable locations of the sera to be analyzed, and c) a large amount (milliliters) of sample required. As to the varying locations, the gel barrier used to separate the liquid phase from the cellular phase, if scanned instead of the liquid phase, no doubt will produce an incorrect evaluation.

Thus, it has been the practice, when dealing with tubes of liquid of unpredictable height, to aliquot into a secondary tube, with added exposure and time, or ascertain where the liquid phase is, such as by LED scanning of the tube contents, as shown, for example, in FIG. 3 of EPA 185,330. Such requirements introduce additional equipment expenses and process delays. This, coupled with the difficulties of spectrophotometrically scanning through the patient label, has rendered such scanning of primary collection containers problematic and expensive.

On the other hand, conventional clinical analyzers using dried slide test elements to test for target substances, require usually at least five minutes to conduct an assay of the target substance, given the need for incubation. With these incubator times, it becomes difficult to obtain throughputs much greater than about 1000 tests per hour. A technique that would allow for much higher throughput in such analyzers is sorely needed.

Thus, there has existed prior to this invention, the need to provide an inexpensive and simple method of spectrophotometric scanning of biological liquids such as blood sera or plasma separated from whole blood, that is, one which eliminates the need to locate the liquid's position in whatever container is used, and the need to scan through an identification label. There is further a need to enhance the throughput of tests in an analyzer that assay target substances.

RELATED APPLICATION

A related application, co-filed herewith by the same inventors, is U.S. Ser. No. 08/814,977, entitled: "Improved Analyzer Throughput Featuring Through-The-Tip Analysis", Attorney Docket No. CDS0133. That application claims a divisible aspect disclosed but not claimed herein, namely a method for improved throughput in which certain analytes are assayed on a dried slide test element after assaying first for analytes other than said certain analytes, by spectrophotometrically scanning the sample liquid in the dispensing tip.

SUMMARY OF THE INVENTION

In accordance with one aspect of the invention, there is provided a new use of an old device, namely the disposable tip of an analyzer aspirator probe, heretofore used to collect and then dispense a biological liquid onto or into a test element, from a primary patient collection container. More specifically, there is provided a new use of tips used in analyzer aspirators to collect biological liquid for dispensing into or onto a test element, comprising the steps of:

a) aspirating a known quantity of the liquid from a supply of the same, into a tip mounted on an analyzer aspirator;

b) inserting the tip with the aspirated liquid, into a light-tight enclosed container;

c) passing through the tip while enclosed, a beam of light of near infrared and adjacent visible wavelengths; and d) spectrophotometrically analyzing the portion of the light transmitted through the tip, by correlating the transmitted light with the concentration of one or more target substances in the liquid.

In accordance with another aspect of the invention, there is provided not just a new use of the conventional tip, but also a novel dispensing station in a clinical analyzer. More specifically, there is provided a dispensing station for use in a clinical analyzer, comprising:

an aspirator probe;

a tip mounted on the probe, for collecting biological liquid from a primary collection tube and for dispensing at least a portion of the collected liquid onto or into a test element;

means for creating a partial pressure or partial vacuum within the probe and the tip;

a spectrophotometer emitting near infrared and adjacent visible radiation and generating a signal responsive to portions of the radiation absorbed by any medium the radiation passes through;

a light-tight enclosure defining a cavity sized to receive the tip while mounted on the probe; and passageways defining radiation paths to and from the enclosure from and to the spectrophotometer, the passageways being constructed to deliver and receive, respectively, the radiation for transmission through the tip when the tip is in place in the cavity, so that liquid in the tip can be irradiated by the radiation to determine concentration of target substances therein.

Accordingly, it is an advantageous feature of the invention that spectrophotometric analysis can be made of blood serum or plasma, following centrifugation, without having to a) locate the position of the serum or plasma in the container, or b) scan through an identification label.

It is a related advantageous feature of the invention that such spectrophotometric analysis is rendered in a simpler and less expensive manner, than is the case when scanning primary patient collection tubes.

Yet another advantageous feature is that much smaller volumes of patient sample can be used for the test, than are possible using primary patient collection containers.

Yet another advantageous feature is that results are achieved in less time since no incubation time is required for the spectrophotometric analysis.

Other advantageous features will become apparent upon reference to the following description, when read in light of the attached drawings.

DESCRIPTION OF THE PREFERRED EMBODIMENTS

The invention is hereinafter described in connection with preferred embodiments, in which a preferred (and conventional) translucent disposable tip is used on a preferred (and conventional) analyzer aspirator, and a preferred light-tight enclosure connected to the spectrophotometer by passageways using fiber optics, to analyze for targets representing patient sample quality in blood serum or plasma. Additionally, however, the invention can be used regardless of the type of translucent or transparent tip, aspirator, liquid, or light-tight enclosure that is used, regardless of the optical system providing passageway of the light to and from the spectrophotometer, and regardless of the target substance being detected, so long as the target has sufficient NIR and adjacent visible radiation absorption. That is, the target substance can be a traditional substance tested for concentration in an analyzer heretofore on a slide test element, for example, albumin or glucose. The liquid can be whole blood, urine or cerebral spinal fluid as well. Also, the tip can be permanent rather than disposable, and an open lens system could be used in place of fiber optics, to focus the light to the light-tight enclosure and then to the detecting station.

Not shown herein nor described in any detail is the spectrophotometer used with the invention. The reason is that any spectrophotometer is useful, provided it generates and detects via transmission, radiation emitted in the near infrared and adjacent visible light regions with sufficient spectra precision. As used herein, "near infrared and adjacent visible" means, radiation between about 400 and 2500 nm, and most preferably, between about 475 and 1075 nm. These wavelengths are advantageous as they provide sufficient spectral penetration of the disposable tip as well as sufficient spectral absorption from target analytes. 475 nm is considered to be particularly useful for bilirubin detection by this invention. Useful materials for the tips that allow desired spectral penetration are those commonly used to manufacture disposable tips (polypropylene or polyethylene).

Also as used herein, "spectrophotometric" means a technique that captures the spectral response over a range of wavelengths and correlates a response for each wavelength in the range. In contradistinction, "photometric" means an analysis of light radiation to correlate a response to only a particular wavelength. A "spectrophotometer" then is the apparatus that does this spectrophotometric analysis.

Also, as used herein, "primary patient collection container" means, a container in which patient biological liquid, usually blood, is placed initially, with a label, and processed to prepare the desired sample liquid for testing. In the case of whole blood, such processing includes phase separation in which liquid serum or plasma is separated from the cellular phase comprising the blood cells, usually with a gel separation barrier.

Further, as used herein, a "test element" means any reaction vessel in which at least one reagent has been pre-supplied, for example so-called dried slide test elements such as are described in, e.g., U.S. Pat. No. 3,992,158; or a cup or well having a cavity pre-coated with one or more anti-bodies, such as is described in U.S. Pat. No. 5,441,895, or an uncoated cavity to which reagent is added.

Further as used herein, "light tight" means, effective to exclude ambient light by an amount such that no more than about 10 percent of the detected light is due to the exterior ambient light.

Still further as used herein, "icteric" means the condition wherein high levels of bilirubin and/or biliverdin are present in the sample.

No details are provided as to the mathematical analysis involved in correlating the amount of transmission of the near infrared and adjacent visible radiation through the biological liquid, with the concentration of the target substance. The reason is that such is well-known, as is evident from Canadian Patent No. 2,019,511; the article in *Clin. Chem.*, Volume 38, Pages 1623–1631 (1992); and the tutorial articles in *Anal. Chem.*, Volume 59, Number 17, Pages 1007A–1017A (September 1987) and *Anal. Chem.*, Volume 66, Number 15, Pages 795A–804A (August 1994).

Figure 1:
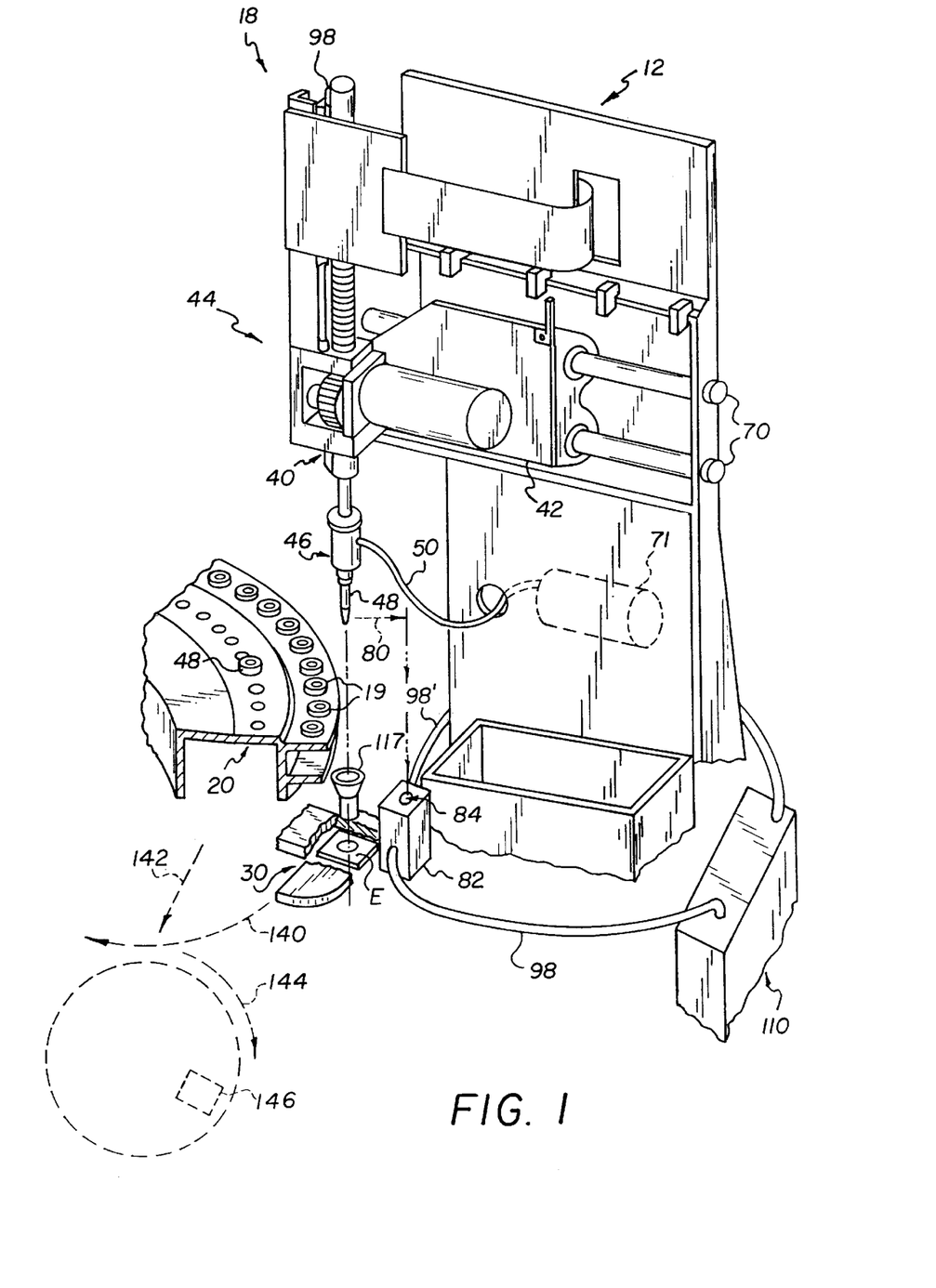
FIG. 1 is a fragmentary isometric view of an analyzer aspirator probe, illustrating the location of the scanning block of FIGS. 2A and 2B in the rest of a conventional analyzer.

FIG. 1 illustrates a conventional analyzer 12 utilizing the current invention. It is conventional to utilize a dispensing station 18 to collect by aspiration, a sample of biological liquid, e.g., serum or plasma, from a supply comprising primary collection containers 19 in tray 20, into a disposable tip 48 mounted on aspirator probe 46. The sample liquid is subsequently dispensed onto a slide test element E held at a slide distributor 30 and obtained from a source of test elements, not shown. Control of the dispenser 40 providing probe 46 is via the mechanisms such as vertical drive 44 and carriage 42 mounted on support rods 70, all as described in, e.g., U.S. Pat. No. 4,340,390. A conventional pump 71 of any kind is used as the means for creating a partial vacuum or partial pressure within tip 48.

In accordance with one aspect of the invention, a new use is made of tips 48 besides simply, the collection by aspiration, of liquid from containers 19, and then subsequent dispensing onto slide test elements E. Tip 48 carrying the sample liquid aspirated into it, is moved, arrow 80, FIG. 1, to a test station 82 prior to placing it in holder 117 for dispensing. Station 82 comprises, as is more clearly shown in FIGS. 2A, 2B, and 3, a scanning block that is an effective light-tight enclosure having a cavity 84 sized to receive a tip 48. Preferably, cavity 84 comprises an upper portion 86, FIG. 3, a lower portion 88 of smaller inside diameter than portion 86, a ledge 90 of demarcation between the upper and lower portions, an air vent 92 in ledge 90, a conical exit port 94 extending from the lower portion away from the upper portion, and two passageways 96 adapted to receive fiber optics 98,98' to and from portions of a spectrophotometer. Exit port 94 is shaped generally with the shape of the exit orifice portion of tip 48, hence its conical shape for this preferred tip 48. An optional air tube 100 is connected to exit port 94 to reduce the potential of pumping fluid out of the tip. If the tube is also opaque, an option, then it also helps to eliminate light leakage up into the tip.

Fiber optics 98,98' are connected to a spectrophotometer, FIG. 1, comprising a light source 110 and a detector combined into a single unit 110, which is conventional.

For maximum efficiency, station 82 is effectively light-tight as defined herein so that the light passing to the detector is at least 90% of that transmitted through tip 48 from fiber optic 98. There are several ways in which this can be achieved.

Figure 2A:
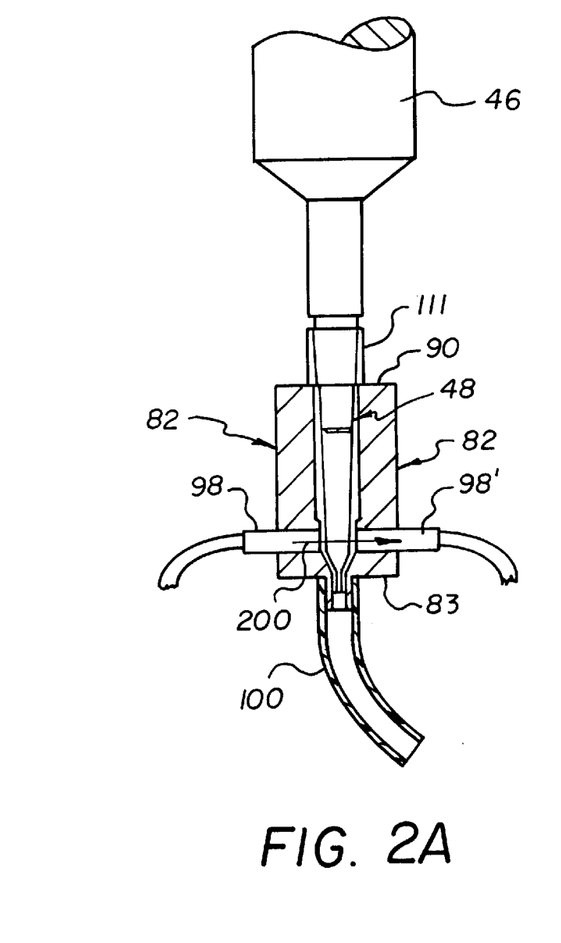
FIGS. 2A and 2B are alternative fragmentary elevational views in mid-section of the apparatus providing two alternative embodiments of the invention.

First, for a station 82 as shown in FIG. 2A, comprising block 83 having an upper surface 90 that acts as the support shoulder for the enlarged upper portion 111, and hence goes no higher than that, and a side clearance of about 0.5 mm between tip 48 and block 83, the light leakage that occurs is corrected for by taking a blank reading (with the fiber 98 delivering no light) at the same ambient light conditions as is used when NIR and adjacent visible radiation is delivered by fiber optic 98. The blank reading is then subtracted from the sample reading and reference reading.

Figure 2B:
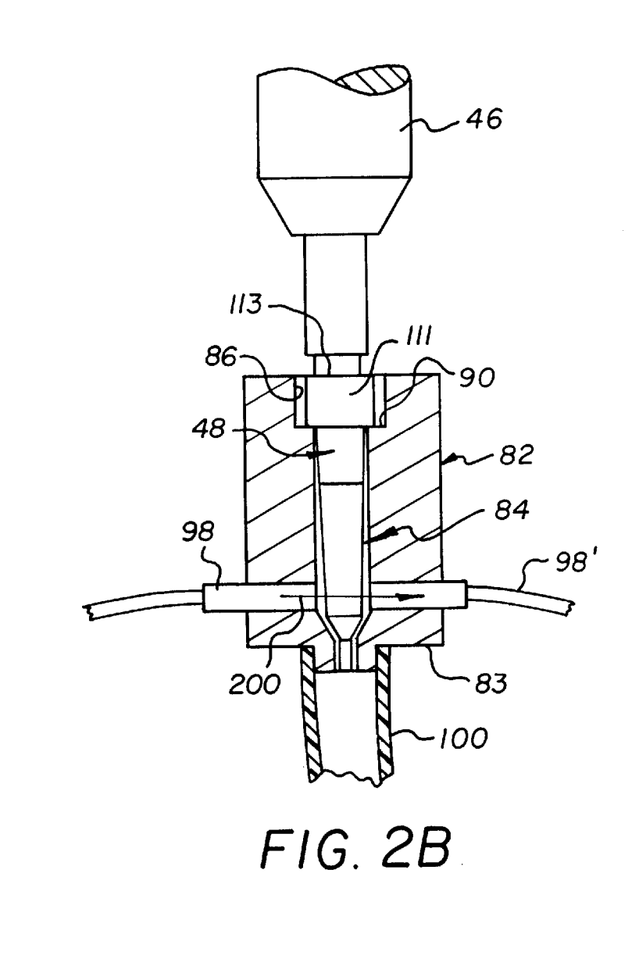

Alternatively, if a subtracted blank reading is not to be used, and the side clearance is still the same as noted above, the same light tightness can be achieved by extending the height of block 83 up to at least the height of the top surface 113 of upper portion 111 of tip 48, FIG. 2B.

Because the seating of tip 48 on shoulder surface 90 is an effective seal, it is preferable that some air release be provided between upper and lower portions 86 and 88 as tip 48 is inserted and withdrawn. That is the function of vent 92, FIG. 3. This vent allows the release of the increase in pressure created when a tip is inserted into station 82, so that a bubble of air is not forced into the liquid of the tip to possibly interfere with the light-scanning of the liquid. Likewise, when tip 48 is withdrawn after having been light-scanned, vent 92 prevents a vacuum being created such as could draw out of tip 48, a portion of the sample liquid which then contaminates the station 82 for subsequent tips and samples.

Figure 3:
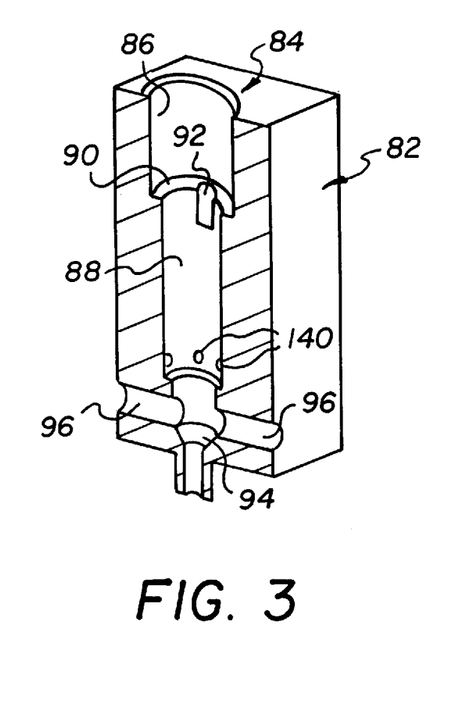
FIG. 3 is an isometric view, partially broken away at its mid-section, of the station 82 of FIG. 2A, showing the air vent that prevents both a pulse of upward pressure from occurring when the tip is inserted, and suction on the end of the tip when the tip is removed.

To further assist in centering tip 48 within cavity portion 88 between fiber optics 98 and 98', locator bumps 140 can be disposed, FIG. 3, near the bottom of portion 88 above passageways 96.

In use, tip 48 is inserted into station 82 before insertion into holder 116. While at station 82, a beam of NIR and adjacent visible wavelengths as defined above, is passed through the tip and its liquid so that transmitted radiation is spectrophotometrically analyzed at spectrophotometer 110. The signal produced by the detector is then correlated with the concentration of target substances. A preferred set of target substances is those that measure sample quality, specifically those selected from the group consisting of hemoglobin, lipids, bilirubin (BR), and biliverdin (BV), as shown in the examples below. However, any target substances capable of spectrophotometric detection by its absorption spectra, can be correlated and detected by this invention. More specifically, certain assays that heretofore have been conducted in slide test element E, can be conducted spectrophotometrically through the tip, as described hereinafter.

Thereafter, the tip is withdrawn and inserted into holder 116 at which point the sample liquid is dispensed onto slide test element E conventionally containing one or more reagents to ascertain the concentration of an analyte in the sample liquid, as is well-known.

As will be readily evident, the tips 48 used herein allow transmission of NIR and adjacent visible radiation, and most preferably 475 to 1200 nm, and preferably are free of labels, since any labeling is done exclusively on primary containers 19. Materials useful for this purpose include polypropylene and polyethylene.

Figure 4A:
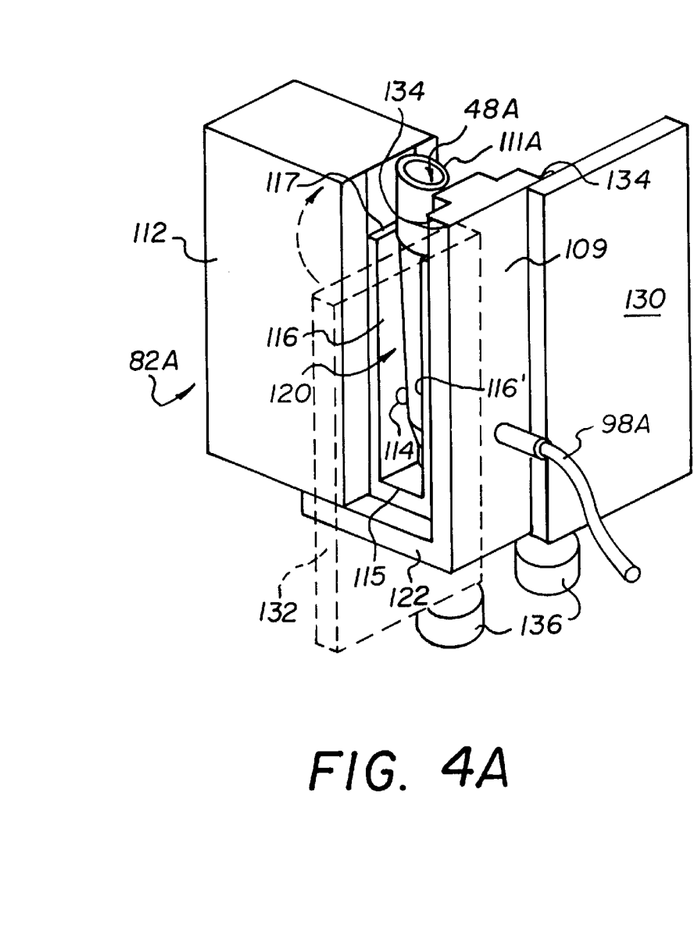
FIGS. 4A and 4B are fragmentary isometric views of other alternative embodiments of the invention.
Figure 5:
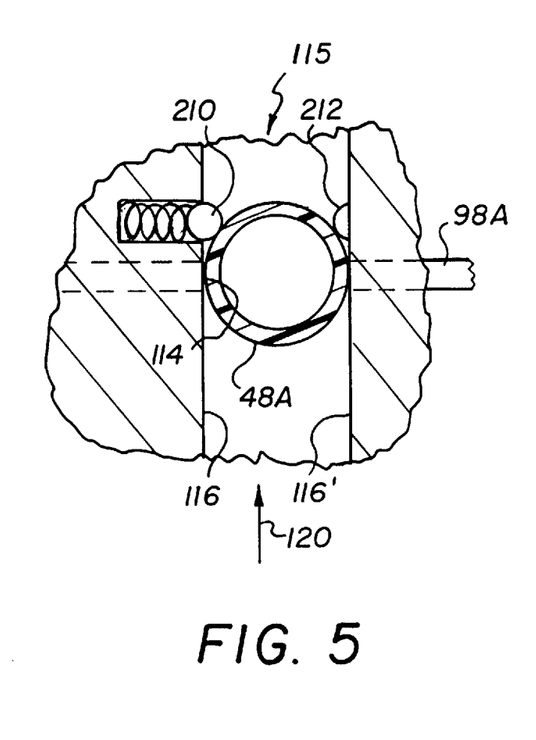
FIG. 5 is a plan view in section of a portion of the structure of FIG. 4, illustrating a mechanism for locating tip 48A.

It is not necessary that test station 82 be constructed as a solid block with only a cavity for the disposable tip and apertures for the fiber optics, or that the tip be lowered into the same. Instead, side walls of station 82 can be opened and closed, to provide a slot that allows pass-through of the tip, as shown in FIGS. 4A and 5. Parts similar to those previously described bear the same reference numeral, to which the distinguishing suffix "A" has been appended.

Thus, station 82A comprises two fixed, opposed segments 109,112 spaced a distance apart. Each segment has an opposing face, 116,116' that defines a slot 115 between them. Top surface 117 of faces 116,116' provide a guide rail and seat for upper portion 111A of tip 48A. Segment 109 has a fiber optic 98A penetrating it from a light source, not shown, whereas segment 112 has a sensor 114 in face 116 that is connected to a spectrophotometer built into or connected with segment 112.

The opposing faces of segments 109 and 112 define slit 115 with a spacing distance that allows a disposable tip 48A to slide through, arrow 120. Those opposing faces can be spaced apart a fixed distance for the sliding of tip 48A.

Because segments 109 and 112 create slot 115 for the through-passage, arrow 120, of tip 48A, with an aspect ratio much smaller than that described above for the vertical aperture 84, it is preferred to close slot 115 for the spectrophotometric measurement. To that end, pivoting doors 130, 132 are hingedly attached at 134 to opposite edges of segment 109, of sufficient width to close off slot 115 when they are pivoted, arrows 136,138 to their closed positions (not shown). (Door 132 is shown in phantom for clarity only.) To pivot the doors, preferably the pintle of hinges 134 is attached or affixed to a rotating drive shaft (not shown), of conventional motors 136.

Alternatively, doors 130 and 132 can be omitted by lengthening slot 115 so that it has an aspect ratio in the horizontal direction that is comparable to the vertical aspect ratio stated for cavity 84 above.

To assist in stopping the lateral movement, arrow 120, of tip 48A just precisely at fiber optic 98A and detector 114, FIG. 5, a spring-biased detent 210 is preferably located in face 116, cooperating with a fixed projection 212 on opposite face 116'. Detent 210 is pushed by the tip into face 116 when it is time, after the reading, to move tip 48A out of slot 115 in the direction of arrow 120. As noted in the previous embodiment, tip 48A allows transmission of the NIR and adjacent visible wavelengths used.

Figure 4B:
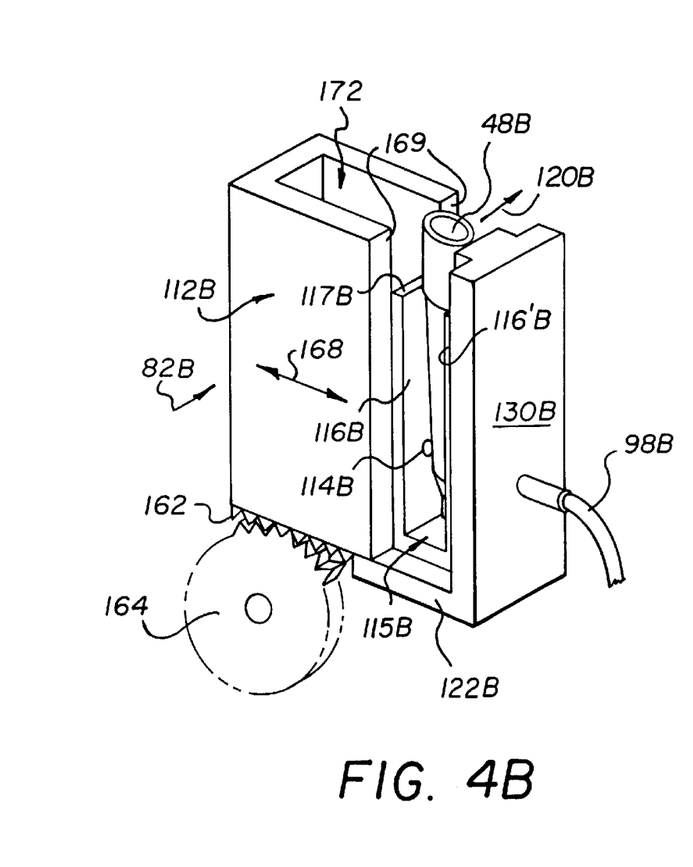

Alternatively, FIG. 4B, segment 112B can be movably mounted on plate 122B to close off light leakage. Parts similar to those previously described bear the same reference numeral, to which the distinguishing suffix "B" is appended. Thus, station 82B comprises plate 122B forming with faces 116B and 116'B a U-shaped slot that allows a tip 48B to slide through, arrow 120B, while supported on top surfaces 117B. Fiber optic 98B delivers light through stationary segment 130B, and sensor 114B in stationary face 116B delivers light to a spectrophotometer, not shown.

To close the light leakage that can occur through the U-shaped slot of plate 122B and faces 116B and 116'B, segment 112B is mounted to slide on plate 122B as driven by a rack 162 and a drive pinion 164, arrow 168, thus opening or closing off the slot. When closed, face 116B and tip 48B occupy the space 172 within segment 112B, and wall portion 169 closes off slot 115B.

In addition to testing for patient sample quality, any target substance that is analyzable spectrophotometrically using NIR and adjacent visible wavelengths, can be analyzed by spectrophotometer 110 while the patient sample is in tip 48A. These include hemoglobin, albumin, and glucose, among others. By testing these target substances in the tip, it is not necessary, and indeed the analyzer preferably skips, further assays for them when the sample is deposited onto slide test element E. This enhances greatly the total throughput of the analyzer, inasmuch as the spectrophotometric detection through the tip requires only about 4 seconds for all the target substances so analyzed, compared to about 4 seconds for each separate assay done on a slide test element E. "Time to result" is also drastically improved by the spectrophotometric analysis through the tip—4 seconds for through-the-tip, compared to 5 minutes on a slide test element.

As an example of the enhanced throughput, the following is a calculation of the advantages that can be achieved on an analyzer such as is available from Johnson & Johnson Clinical Diagnostics under the trademark "VITROS 950" analyzer. This assumes 1) that dispensing of sample liquid onto a slide test element is the limiting step in the analysis, and that this involves 8 seconds to aspirate, 4 seconds to dispense onto a test element and load the element into the distributor of the VITROS 950 analyzer, and that all, and only, calorimetric analysis is done in the tip by this invention.

If the mix of chemistries to be run is zero potentiometric, 7 colorimetric and zero rates, then without the invention the throughput is 300 test elements per hour. With the invention, it can, be shown to be about 2100 per hour, which is a 7-fold increase. If on the other hand there are only 5 calorimetric tests, and either 2 rate or 2 potentiometric tests to be conducted, then the throughput without the invention should be about 420 per hour, and about 1050 per hour with the invention, for a 2.5-fold increase. Still further, if the mix of seven chemistries is such that there are only 3 colorimetric and 4 potentiometric tests to run, there is no increase in throughput obtained by doing this invention (525 tests per hour in both cases.)

Testing of such analytes in this manner while in the tip is preferably done with some kind of temperature control of the sample liquid. This need not be done only by controlling the temperature at test station 82, but can also be done by heating or cooling the sample liquid in containers 19, FIG. 1, or while the liquid is in the tips 48, etc., but not at station 82.

Nevertheless, there will still be some assays that require the use of slide test element E. The process is schematically illustrated in FIG. 1. Tip 48 is inserted into holder 117 and a portion of the patient sample is dispensed onto slide test element E. Thereafter, distributor 30 is rotated, arrow 140, to a position in which test element E is linearly transferred, arrow 142, to an incubator (not shown) within which it rotates, arrow 144, until it is read or detected at a test station 146, all as is well-known and conventional. Test station 146 conventionally comprises a colorimetric or potentiometric detector, in contrast to the spectrophotometer 110 used with tips 48,48A.

Although as noted above, tests conducted at station 146 preferably skip those done through the tip, it is also possible to repeat at station 146 such spectrophotometric assays, to obtain a "check" on the accuracy of the latter.

It is also contemplated that the order of testing can be reversed—that is, a portion of the sample liquid can be deposited on a test slide as described above, before doing the measurements through-the-tip at the NIR and adjacent visible wavelengths.

EXAMPLES

The following non-exhaustive tests were run to demonstrate the invention:

The apparatus of FIG. 2 was used, in which a disposable tip available from Johnson & Johnson Clinical Diagnostics, Inc., under the trademark "Vitros", heretofore known as the "Ektachem" disposable tip, was used. The optical fibers were 0.2 mm single fibers, connecting station 82 via the fibers 98 and 98', to a "TC 2000" dual beam, in-time spectrophotometer that uses a linear diode array detector, available from CME Telemetrix, using a tungsten-halogen light bulb light source 110 as detector 112. Diffraction gratings were used at detector 112 to allow only radiation of 580 to 1100 nm to be detected. (The reference beam portion of the spectrophotometer has been omitted for clarity.) The amount of liquid aspirated into tip 48 was 50 μL, so that the liquid level was well above the pass-through arrow 200, FIG. 2. Testing has demonstrated that only 30 μL is needed.

The liquids tested were, first as calibrators, a randomized set of liquids comprising known amounts of hemoglobin, Intralipid™ (a fat emulsion which mimics naturally occurring chylomicrons) available from Pharmacia, Inc.), and biliverdin all spiked onto a human serum matrix.

The following Table 1 sets forth the levels of Hb, IL, and BV in serum after spiking. "Hb" means hemoglobin, "IL" means Intralipid, "BV" means biliverdin dihydrochloride, and "BR" means bilirubin.

TABLE 1

| Sample Number | g/L Hb | g/L IL | mg/dL BV |
|---|---|---|---|
| 1 | 0.56 | 0.00 | 0.00 |
| 2 | 0.83 | 0.00 | 0.00 |
| 3 | 1.11 | 0.00 | 0.00 |
| 4 | 1.38 | 0.00 | 0.00 |
| 5 | 1.65 | 0.00 | 0.00 |
| 6 | 1.91 | 0.00 | 0.00 |

TABLE 1-continued

| Sample Number | g/L Hb | g/L IL | mg/dL BV |
|---|---|---|---|
| 7 | 2.17 | 0.00 | 0.00 |
| 8 | 2.43 | 0.00 | 0.00 |
| 9 | 2.69 | 0.00 | 0.00 |
| 10 | 2.95 | 0.00 | 0.00 |
| 11 | 1.19 | 0.00 | 0.00 |
| 12 | 1.77 | 0.00 | 0.00 |
| 13 | 2.35 | 0.00 | 0.00 |
| 14 | 2.93 | 0.00 | 0.00 |
| 15 | 3.50 | 0.00 | 0.00 |
| 16 | 4.06 | 0.00 | 0.00 |
| 17 | 4.62 | 0.00 | 0.00 |
| 18 | 5.17 | 0.00 | 0.00 |
| 19 | 5.71 | 0.00 | 0.00 |
| 20 | 6.26 | 0.00 | 0.00 |
| 21 | 0.54 | 1.00 | 0.83 |
| 22 | 0.79 | 1.97 | 0.41 |
| 23 | 1.01 | 2.83 | 1.17 |
| 24 | 1.22 | 1.14 | 3.77 |
| 25 | 1.50 | 1.63 | 2.32 |
| 26 | 1.73 | 2.30 | 1.91 |
| 27 | 2.03 | 1.42 | 1.57 |
| 28 | 2.25 | 0.47 | 2.70 |
| 29 | 2.46 | 0.68 | 3.03 |
| 30 | 2.54 | 3.00 | 3.21 |
| 31 | 1.14 | 2.00 | 1.66 |
| 32 | 1.69 | 3.94 | 0.82 |
| 33 | 2.13 | 5.61 | 3.10 |
| 34 | 2.59 | 2.27 | 7.55 |
| 35 | 3.19 | 3.26 | 4.63 |
| 36 | 3.68 | 4.61 | 3.82 |
| 37 | 4.36 | 2.86 | 2.37 |
| 38 | 4.78 | 0.93 | 5.40 |
| 39 | 5.22 | 1.37 | 6.06 |
| 40 | 5.40 | 6.01 | 6.41 |

A second set of 21 liquids similarly prepared, were prepared to have the components of Table 2, and treated as unknowns.

TABLE 2

| Sample Number | g/L Hb | g/L IL | mg/dL BV |
|---|---|---|---|
| 1 | 0.34 | 2.05 | 3.40 |
| 2 | 0.50 | 2.44 | 4.06 |
| 3 | 0.66 | 2.83 | 4.69 |
| 4 | 0.80 | 3.19 | 5.30 |
| 5 | 3.77 | 3.27 | 5.43 |
| 6 | 1.08 | 3.88 | 6.44 |
| 7 | 1.35 | 1.56 | 3.33 |
| 8 | 1.56 | 1.15 | 1.15 |
| 9 | 5.73 | 3.04 | 2.21 |
| 10 | 1.80 | 3.04 | 1.80 |
| 11 | 4.75 | 3.54 | 1.31 |
| 12 | 2.12 | 2.60 | 2.16 |
| 13 | 2.18 | 4.13 | 2.74 |
| 14 | 2.58 | 0.46 | 0.76 |
| 15 | 5.26 | 1.55 | 4.50 |
| 16 | 2.68 | 1.26 | 5.56 |
| 17 | 2.83 | 0.83 | 6.23 |
| 18 | 0.00 | 2.38 | 0.00 |
| 19 | 1.79 | 0.00 | 0.00 |
| 20 | 0.00 | 0.00 | 3.95 |
| 21 | 0 | 0 | 0 |

Figure 6:
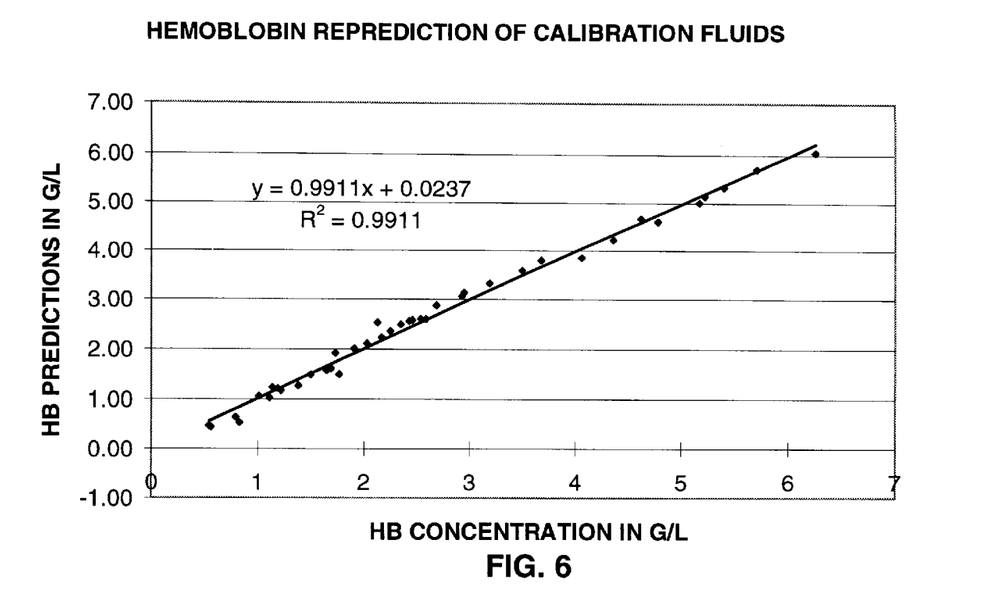
FIGS. 6 through 11 are regression plots of test samples scanned and analyzed spectrophotometrically in accordance with the invention, for levels of hemoglobin, lipemia, or icteric nature of the sample.

The first set of liquids was irradiated as described above to create a calibration algorithm using conventional spectrophotometric practice, and the values of Hb detected in this measurement were plotted against the actual values, FIG. 6, to obtain a regression plot. A variety of calibration algorithms is useful. The following equations are exemplary only:

1) $Hb(g/l) = C_1(dA_{600}/d\lambda_{600}) - C_2(dA_{663}/d\lambda_{663}) - C_3$
2) $IL(g/l) = C_4(dA_{874}/d\lambda_{874}) + C_5$
3) $BV(mg/dL) = C_6(dA_{724}/d\lambda_{724}) - C_7(dA_{803}/d\lambda_{803}) + C_8$ where $A_{600}$ is the absorbance at 600 nm, $\lambda_{600}$ is the 600 nm wavelength, and so forth for the other $A+\lambda$ values, $(dA_i/d\lambda_i)$ is the first derivative of absorbance versus wavelength and $C_1, \ldots C_9$ are constants preferably having the following values:

| | |
|---|---|
| $C_1 = 15.892$ | $C_5 = 0.244$ |
| $C_2 = 15.882$ | $C_6 = 98.068$ |
| $C_3 = 0.21$ | $C_7 = 122.732$ |
| $C_4 = 252.155$ | $C_8 = 0.0685$ |

The regression correlation coefficient $R^2$ in the case of FIG. 6 was 0.991.

Figure 7:
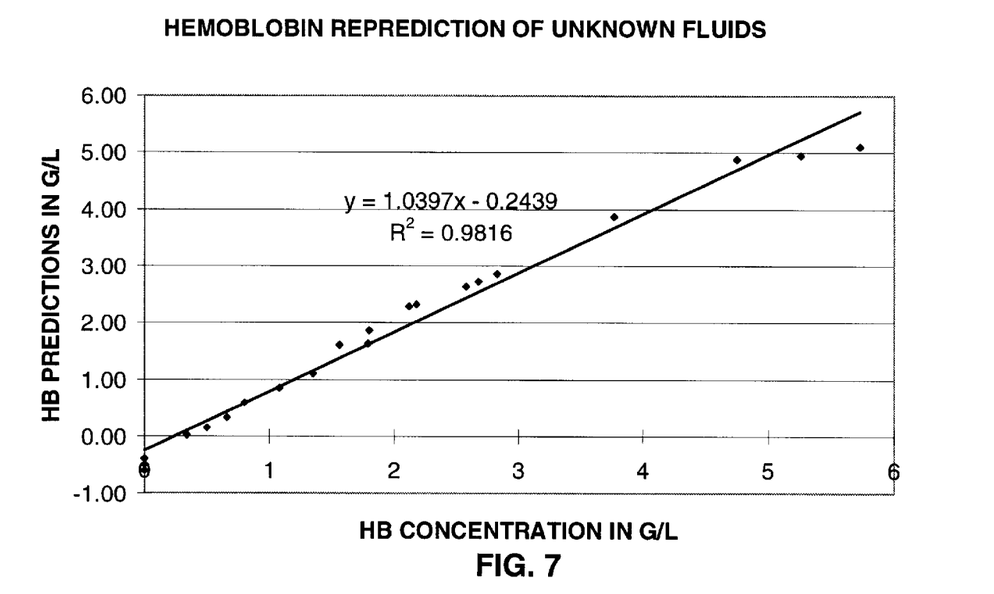

The second set of liquids was then irradiated as described above and the predicted values plotted against their known results, FIG. 7, using the calibration algorithm derived from the first set of liquids, FIG. 6. The $R^2$ value of 0.982 was excellent. This accuracy is adequate to allow the results to be relied upon for clinical assay of Hb in unknown samples, in place of testing on a slide test element.

Figure 8:
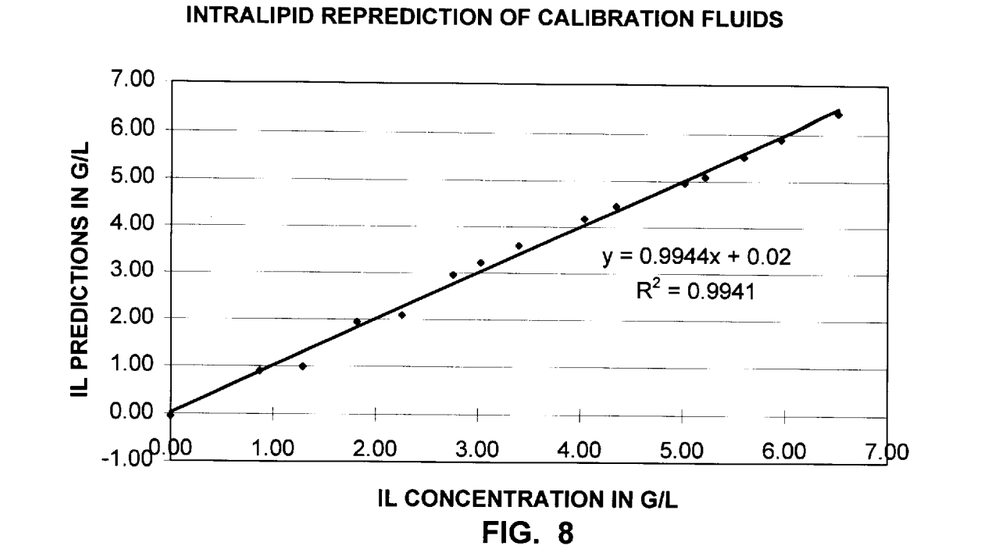
Figure 9:
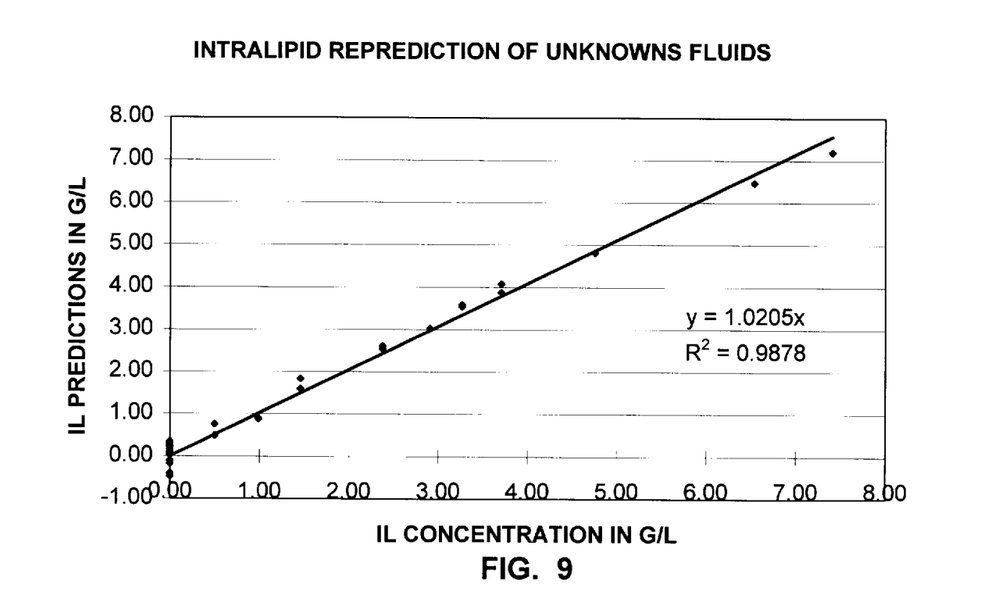

In a like manner, the spectra detected as noted above was evaluated for IL. The calibration results appear in FIG. 8, and the prediction results in FIG. 9. $R^2$ in this case was, respectively, 0.9941 and 0.9878.

Figure 10:
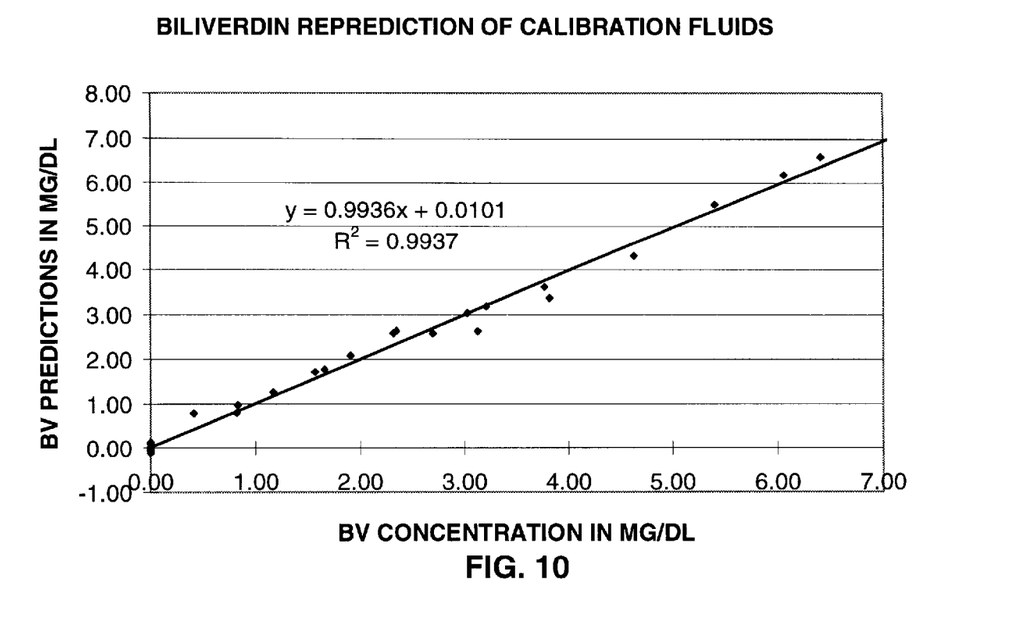
Figure 11:
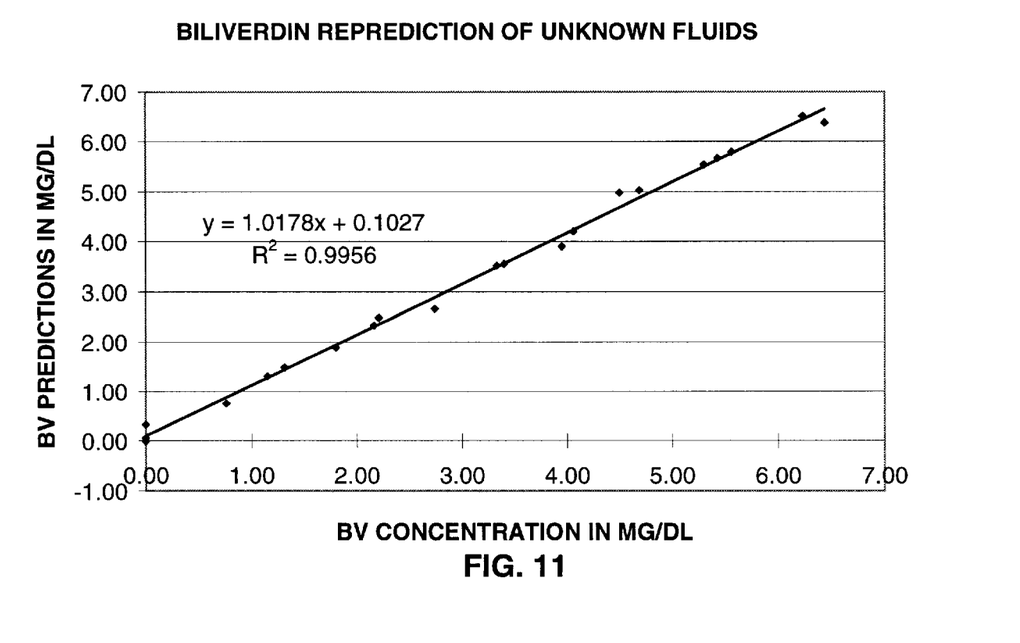

Again, the spectra noted was evaluated, but this time the analysis was for BV. FIG. 10 shows the calibration results, and FIG. 11 the prediction results with $R^2$ being as indicated.

A new, third set of liquids was prepared to illustrate the invention in the detection of bilirubin, and the calibrator version of that set was composed as follows:

| Sample Number | BR mg/dL | Hb g/L | IL gL | BV mg/dL |
|---|---|---|---|---|
| 1 | 8.33 | 0.65 | 0.00 | 0.00 |
| 2 | 8.33 | 0.65 | 0.00 | 0.00 |
| 3 | 0.00 | 1.92 | 0.00 | 0.00 |
| 4 | 0.00 | 1.92 | 0.00 | 0.00 |
| 5 | 34.79 | 0.91 | 0.00 | 0.00 |
| 6 | 34.79 | 0.91 | 0.00 | 0.00 |
| 7 | 23.41 | 1.53 | 0.00 | 0.00 |
| 8 | 23.41 | 1.53 | 0.00 | 0.00 |
| 9 | 31.49 | 0.31 | 0.00 | 0.90 |
| 10 | 31.49 | 0.31 | 0.00 | 0.90 |
| 11 | 37.33 | 1.17 | 0.00 | 1.72 |
| 12 | 37.33 | 1.17 | 0.00 | 1.72 |
| 13 | 22.15 | 0.00 | 0.93 | 0.00 |
| 14 | 22.15 | 0.00 | 0.93 | 0.00 |
| 15 | 0.00 | 0.00 | 2.15 | 0.00 |
| 16 | 0.00 | 0.00 | 2.15 | 0.00 |
| 18 | 17.02 | 0.00 | 0.00 | 8.74 |
| 19 | 17.02 | 0.00 | 0.00 | 8.74 |
| 20 | 33.31 | 0.00 | 0.00 | 1.80 |
| 21 | 33.31 | 0.00 | 0.00 | 1.80 |
| 22 | 25.02 | 0.00 | 0.00 | 5.34 |
| 23 | 25.02 | 0.00 | 0.00 | 5.34 |
| 24 | 29.13 | 0.00 | 0.00 | 3.58 |
| 25 | 29.13 | 0.00 | 0.00 | 3.58 |
| 26 | 13.59 | 0.00 | 0.00 | 7.18 |

The calibration algorithm used for this test was as follows:

4) $BR(mg/dL) = C_9(dA_{495}/d\lambda_{495}) + C_{10}(dA_{512}/d\lambda_{512}) + C_{11}(dA_{578}/d\lambda_{578}) - C_{12}$ wherein the constants were as follows:

$C_9 = -24.878$
$C_{10} = 201.61$ $C_{11}$=44.98
$C_{12}$=6.475

A fourth set of liquids was similarly prepared to check for prediction of the bilirubin values, and that set was comprised as follows:

| Sample Number | BR mg/dL | HB | IL | BV mg/dL |
|---|---|---|---|---|
| 1 | 19.86 | 1.25 | 0.00 | 0.00 |
| 2 | 19.86 | 1.25 | 0.00 | 0.00 |
| 3 | 26.59 | 0.60 | 0.00 | 4.38 |
| 4 | 26.59 | 0.60 | 0.00 | 4.38 |
| 5 | 6.10 | 0.00 | 2.35 | 0.00 |
| 6 | 6.10 | 0.00 | 2.35 | 0.06 |
| 7 | 10.31 | 0.00 | 1.19 | 0.00 |
| 8 | 10.31 | 0.00 | 1.19 | 0.00 |
| 9 | 15.53 | 1.07 | 0.00 | 3.58 |
| 10 | 15.53 | 1.07 | 0.60 | 3.58 |

Figure 15:
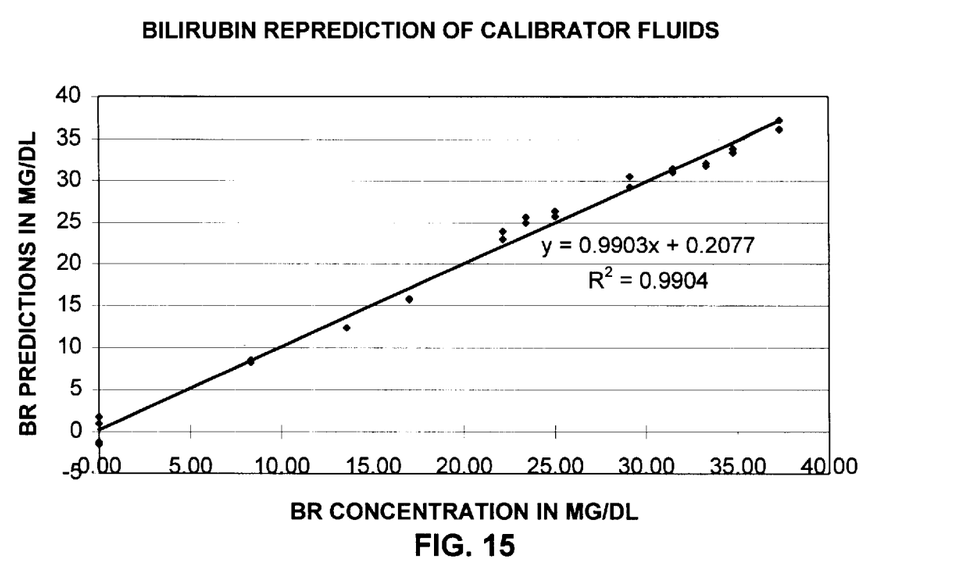
FIGS. 15 and 16 are regression plots of test samples scanned and analyzed spectrophotometrically in accordance with the invention, for levels of bilirubin.
Figure 16:
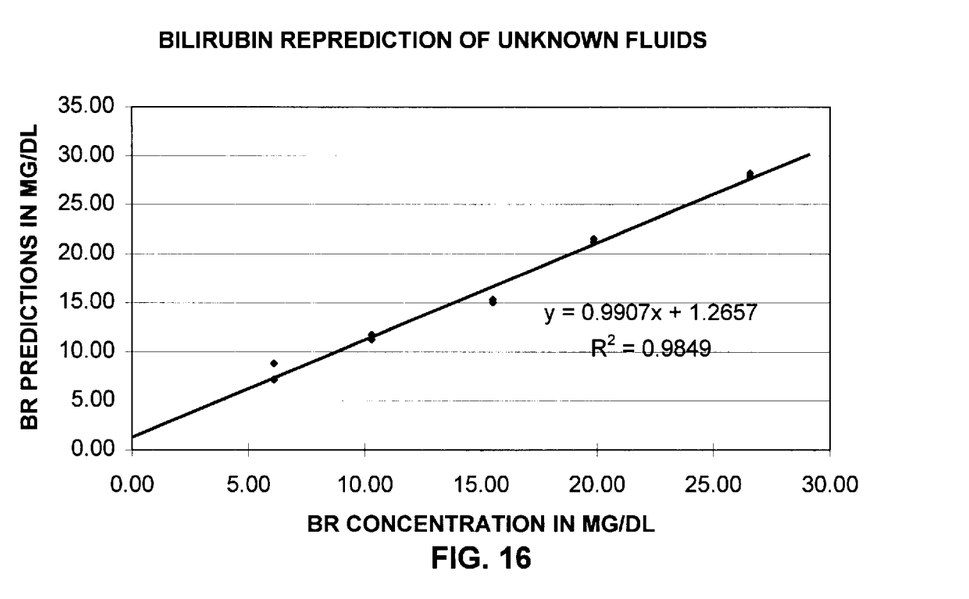

The spectra was evaluated as in the previous examples. FIG. 15 shows the calibration results, and FIG. 16 the prediction results with $R^2$ being as indicated.

For all four experiments (Hb, IL, BV and BR) the results showed excellent correlation such that the results are sufficient to use in place of testing on a slide test element, should any of these be considered a desired assay. In any event, the results clearly allow the biological liquid's sample quality to be ascertained so that the sample can be rejected if determined to be outside the scope of acceptable quality.

As an example of other calibration algorithms that can be used, the following is an alternative to equation number 2 above, for IL:

2') $IL(g/l) = C_{13}(dA_{999}/d\lambda_{999}) + C_{14}(dA_{1051}/d\lambda_{1051}) - C_{15}$, where $C_{13}$=166.068, $C_{14}$=92.352, and $C_{15}$=0.693. When this is used on the first and second set of liquids noted above, $R^2$ becomes 0.988 for the calibration and 0.984 for the prediction. (The actual plots are not shown.)

Figure 12:
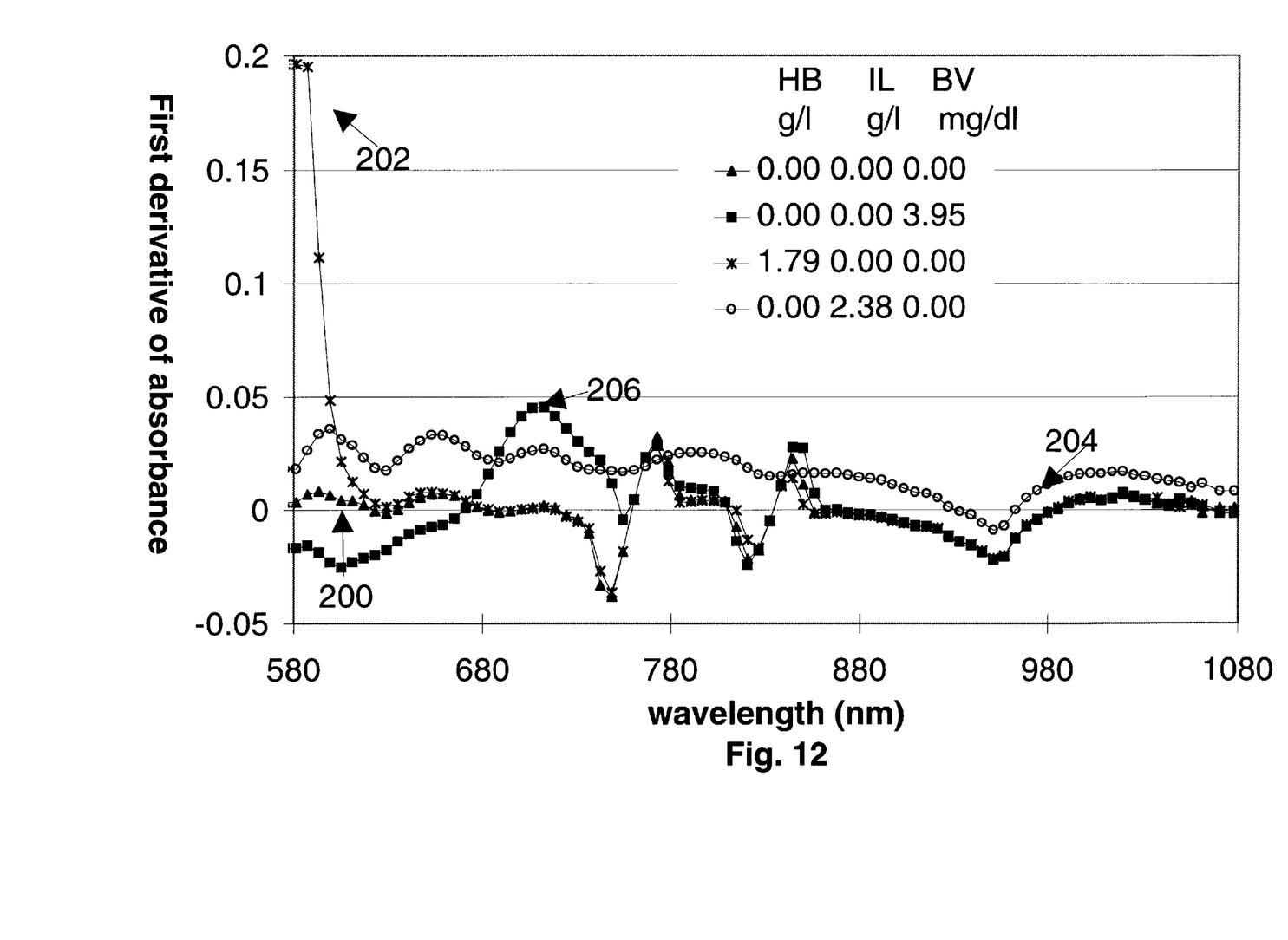
FIG. 12 is a plot of spectral transmissions detected by the invention, showing a sample of each of icterus, hemoglobin and lipids.

FIG. 12 is a plot demonstrating that, in fact, the first derivative of absorbence values in the NIR and adjacent visible spectra does produce sufficient separation, at useful wavelengths, of a sample having either IL, BV, or Hb components present, to allow for independent detection. That is, curve 200 is a sample having none of those components, curve 202 is a sample having only 1.79 g/l of Hb, curve 204 of a sample having only 2.38 g/l of IL, and curve 206 of a sample having only 3.95 mg/dL of BV. Thus, the Hb contributes primarily to the 580–605 nm region of the NIR, IL to the 896–1051 nm region and preferably 896–939 nm, and BV to the 680–750 nm region.

Figure 13:
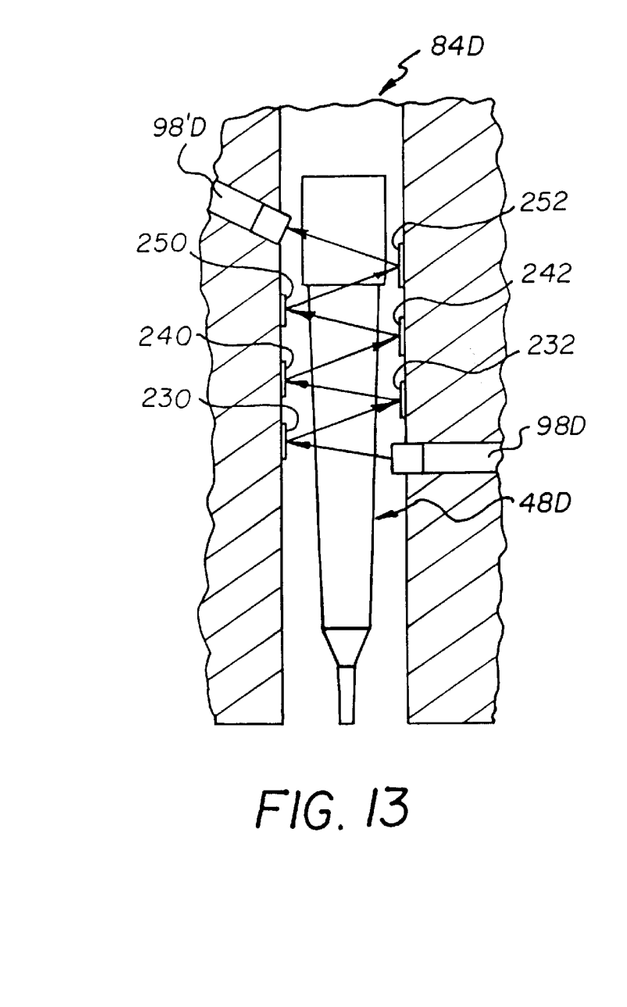
FIGS. 13 and 14 are fragmentary elevational views similar to that of FIG. 2A, but of alternative light-tight enclosure embodiments.

In yet another embodiment, the tip is unchanged from conventional tips, but more than a single pass of the NIR and adjacent visible radiation is achieved through the tip before the absorption spectra is received by the spectrophotometer, FIG. 13. Parts previously described are referred to by the same reference numeral, to which the distinguishing suffix "D" is appended.

Thus, tip 48D is mounted in cavity 84D as before, for irradiation by NIR and adjacent visible radiation emanating from fiber optic 98D, to be received by fiber optic 98'D for processing. However, unlike previous embodiments, receiving optic 98'D is not directly opposite transmitting optic 98D, nor in position to receive the "first pass" radiation. Instead at least one, and preferably three pair(s) of mirrors (230,232; 240,242; and 250,252) are disposed to re-pass the radiation back through tip 48D as many times as there are mirrors. (Six mirrors of the three pairs retransmits the radiation through the tip six times.)

In yet another embodiment, it is not necessary that optics 98,98' (or other versions thereof disclosed above) pass NIR and adjacent visible light through only the thickest part of the tip. Instead, the light can be transmitted through the narrower neck portion. (Parts similar to those previously described bear the same reference numeral, to which the distinguishing suffix "E" is appended.)

Figure 14:
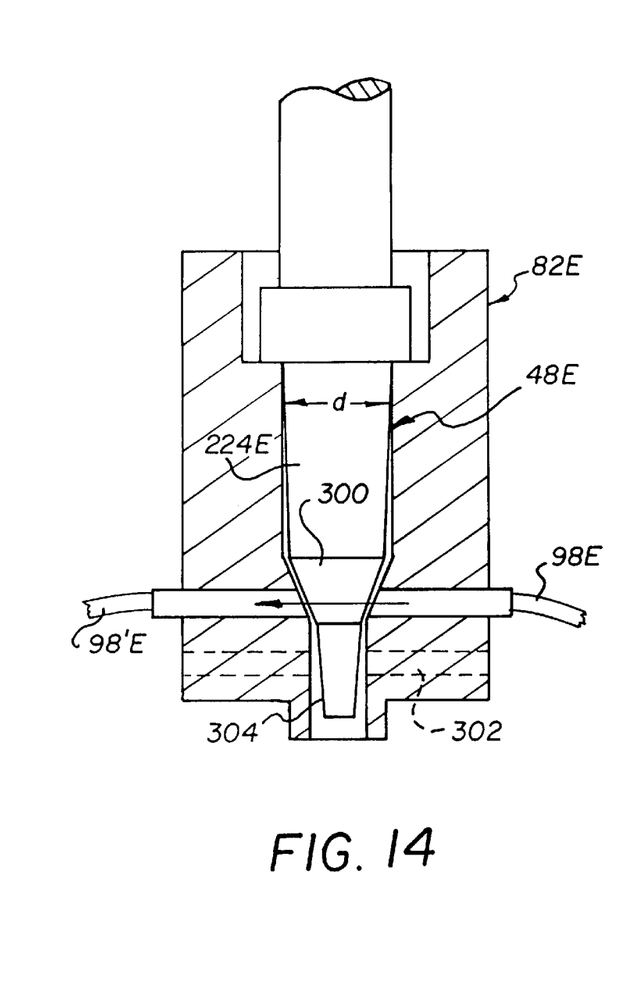

Thus, FIG. 14, illuminating fiber optic 98E is positioned in the block of station 82E so as to illuminate conical neck portion 300 of tip 48E, that has a decreasing diameter compared to diameter "d" of main body portion 224E. The light then transmitted through the tip to receiving fiber optic 98'E passes through much less of the sample. This is desirable if the analyte to be detected is one of high density or has a higher extinguishing coefficient for the NIR and adjacent visible wavelengths in question. In the most extreme cases, fiber optics 98E and 98'E are moved down to the phantom position, 302, that reads through the narrowest part 304 of tip 48E.

Alternatively, passage of the NIR and adjacent visible radiation through the narrower part of the tip can be achieved using previous embodiments, simply by raising the tip (and its probe) sufficiently within station 82, and then illuminating with the NIR radiation. Most preferably, the sequence of steps is as follows: the steps of lowering the tip into a light-tight enclosure comprising an NIR and adjacent visible radiation emitter as shown in any of FIGS. 2A, 2B, 4A, and 4B until the tip is seated therein, scanning the tip and its contents with NIR and adjacent visible radiation emitted from the emitter, and if the contents have a density above a predetermined threshold value, thereafter raising the tip within the enclosure until the emitter is positioned to scan the narrower portion of the tip.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A dispensing station for use in a clinical analyzer, comprising:

an aspirator probe;

a tip mounted on said probe, for collecting a biological liquid from a primary collection container and for dispensing at least a portion of the collected liquid onto or into a test element;

means for creating a partial pressure or partial vacuum within said tip;

a spectrophotometer emitting near infrared and adjacent visible radiation and generating a signal responsive to portions of said radiation absorbed by any medium the radiation passes through;

a light-tight enclosure defining a cavity sized to receive said tip while mounted on said probe, said enclosure including walls and a vent in one of the walls effective to prevent a vacuum from occurring when the tip is removed from the enclosure; and passageways defining radiation paths to and from said enclosure from and to said spectrophotometer, said passageways being constructed to deliver and receive, respectively, said radiation for transmission through said tip when said tip is in place in said cavity, so that liquid in said tip can be irradiated by said radiation to determine concentration of target substances therein.

2. A dispensing station as defined in claim 1, and further including a support for a test element constructed to receive liquid dispensed from said tip, and means for moving said probe and said tip from said enclosure to said support for liquid dispensing after said radiation is transmitted through said tip.

3. A dispensing station as defined in claim 1, wherein said tip is a disposable tip.

4. A dispensing station as defined in claim 1, and further including at least one pair of mirrors disposed within said cavity at a position to intercept radiation transmitted from one of said passageways through said tip in a single pass and to retransmit said radiation back through said tip for the other of said passageways to receive it.

* * * * *